United States Patent [19]

Thompson

[11] Patent Number: 5,651,376

[45] Date of Patent: Jul. 29, 1997

[54] FLEXIBLE DUAL LOOP RESTRAINING DEVICE

[76] Inventor: Greg Thompson, 3400 Highland Farm Rd., Hillsborough, N.C. 27278

[21] Appl. No.: 676,569

[22] Filed: Jul. 8, 1996

[51] Int. Cl.$^6$ .................................................. A61F 5/37
[52] U.S. Cl. ............................................ 128/878; 128/879
[58] Field of Search ................................. 128/846, 869, 128/877, 878, 879; 24/24 PB; 70/16

[56] References Cited

U.S. PATENT DOCUMENTS

| | | | |
|---|---|---|---|
| 4,854,138 | 8/1989 | Charland | 128/878 |
| 4,910,831 | 3/1990 | Bingold | 128/878 |
| 5,088,158 | 2/1992 | Burkholder | 24/16 PB |
| 5,159,728 | 11/1992 | Bingold | 24/16 PB |

*Primary Examiner*—Michael A. Brown
*Attorney, Agent, or Firm*—Rhodes, Coates, & Bennett, LLP

[57] ABSTRACT

An adjustable restraining device includes first and second flexible straps each of which is formed into a loop. The first and second straps are slidably connected to one another to form a dual loop restraining device. Each strap includes a head portion and an opposing end portion. The head portion of each strap includes first and second slots. The loops are formed in each strap by inserting the end portion of the strap through one of the slots. The straps are interconnected with one another by inserting the free end of each strap through a second one of the slots in the head portion of the other strap. When the restraining device is applied to the prisoner, the loops of the device can be drawn closer to one another by grasping and pulling the free ends of the straps.

13 Claims, 4 Drawing Sheets

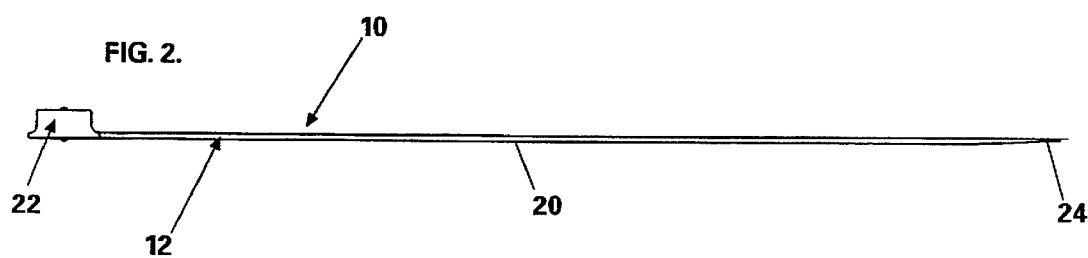
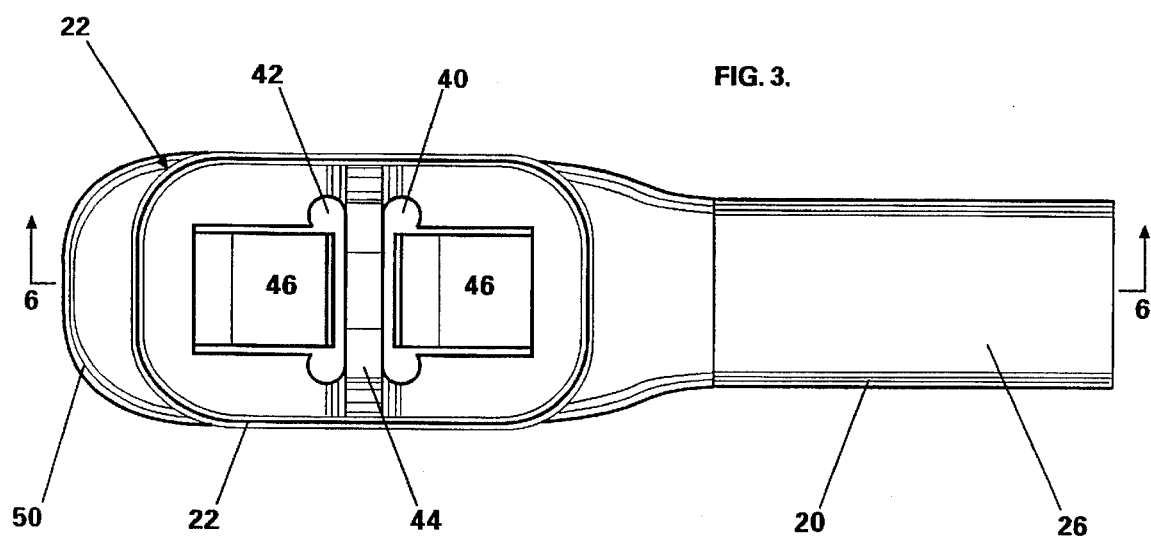

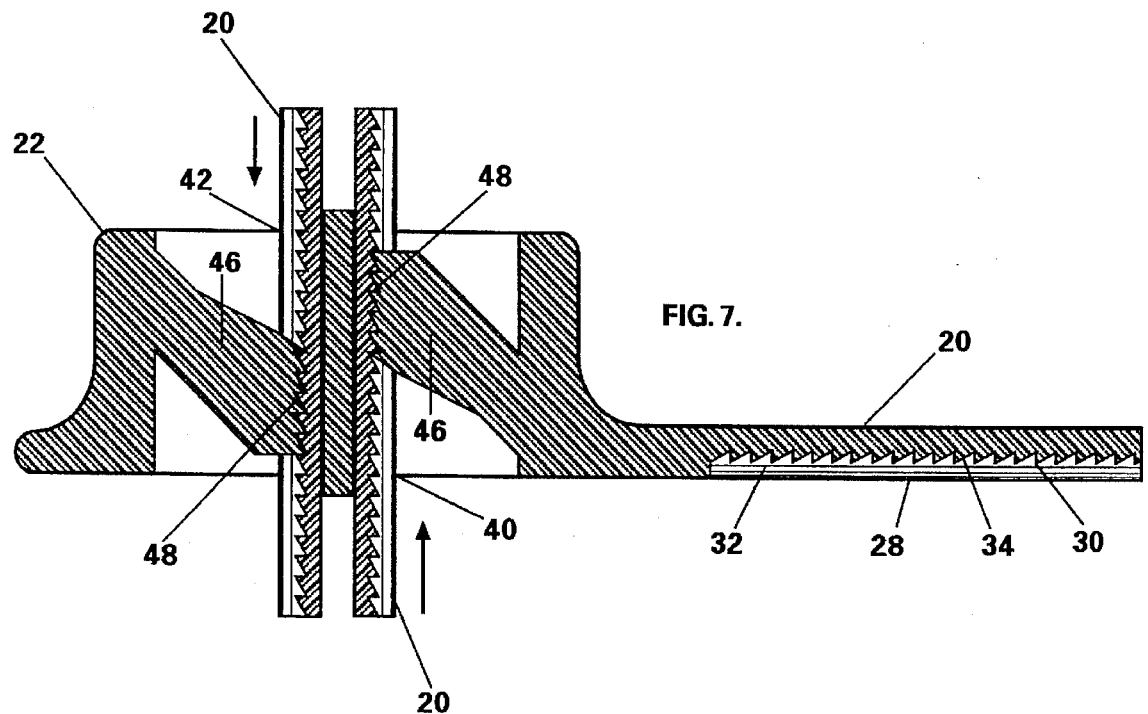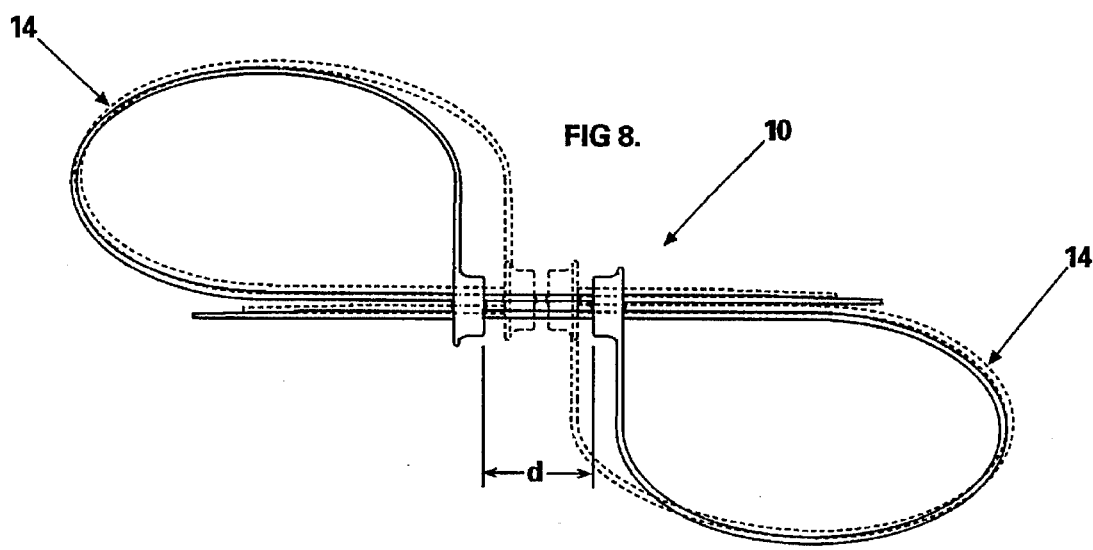

FLEXIBLE DUAL LOOP RESTRAINING DEVICE

FIELD OF THE INVENTION

The present invention relates generally to restraining devices for use by law enforcement officials, and more particularly, to flexible, self-locking restraining ties for binding a prisoner's hands or feet.

BACKGROUND OF THE INVENTION

Conventional restraining devices used by law enforcement officials include handcuffs for restraining a person's hands and leg irons for restraining a person's legs. These types of restraining devices typically comprise two heavy metal cuffs which are secured to one another by chains. The cuffs fit around the prisoner's arms or legs and include some form of locking device to prevent their removal.

There are certain circumstances in which an alternate form of restraining device could be useful. For example, law enforcement officials typically carry on a single pair of handcuffs due to the size and weight of the handcuffs. When the law enforcement officer makes multiple arrests, there is a need for additional restraining devices. It would be impractical for the law enforcement officer to carry a large number of handcuffs.

Another problem encountered when using conventional restraining devices occurs when the prisoner is transferred from one law enforcement agency to another. When the transfer is made, one set of handcuffs and/or leg irons is removed from the prisoner and another set of handcuffs and/or leg irons are applied. Such close contact with the prisoner unnecessarily exposes the law enforcement officers to an attack from a potentially dangerous prisoner.

Various types of disposable restraining devices are known for use by law enforcement personnel. Such restraints typically comprise a flexible strap which can be formed into loops that extend around the prisoner's arms or legs. Representative examples of such devices are shown in U.S. Pat. Nos. 4,910,831; 5,159,728; and 5,443,155. These patents illustrate dual loop restraining devices which use flexible strap-like elements to bind a prisoner's arms and legs. The straps include enlarged head portions having slots through which a free end of the strap is inserted to form the loops. The strap typically includes a series of teeth which are engaged by a pawl in the slot to lock the strap in place and prevent it from being withdrawn.

One limitation associated with the dual-loop restraining devices is that they lack any means to adjust the spacing between the loops. For particularly large and bulky prisoners with limited range of motion, the fixed spacing between loops may not be enough to allow the prisoner's hands to be cuffed behind the prisoner's back. Similar difficulty may be encountered when arresting a person with an injury disability. Also, for a prisoner who poses a safety hazard to the law enforcement officer, it may be desirable to bind his or her hands or feet closely together to reduce the risk associated with the handling of the prisoner. On the other hand, for a prisoner who is cooperative and does not propose a risk to the law enforcement officer, it may be desirable to allow some freedom of movement for the prisoner's comfort.

Accordingly, there is a need for a disposable, strap-like restraining device which allows some adjustment in the distance between the restraining loops.

BRIEF DESCRIPTION OF THE DRAWINGS

FIG. 2 is a side elevational view loop restraining device of the present invention.

FIG. 3 is a plan view of the head portion of one of the strap elements from the side top.

FIG. 7 is a longitudinal section view of the head portion as seen in FIG. 4 with the flexible straps inserted through the slots in the head portion.

FIG. 8 is a plan view of the restraining device 10.

SUMMARY OF THE INVENTION

The present invention is a flexible, dual-loop restraining device which can be employed by law enforcement officers in place of handcuffs or leg irons. The dual loop restraining device of the present invention is formed by two individual strap elements. Each strap element includes a head portion at one end and an opposing insert end. A pair of slots are formed in the head portion of each strap. A pawl is located in each slot which engages teeth formed along the length of the strap to allow one-way movement of the strap through the slots. Each strap is formed into a loop by inserting the free end of the strap through a first one of the slots in the head portion of the same strap. After forming a loop in each strap, the straps with the loops formed therein are interconnected by inserting the free end of each strap through a second one of the slots in the opposing strap. Once the straps are interconnected in this manner, the locking mechanism prevents the straps from being pulled apart.

In use, the restraining device is applied to the arms or legs of a prisoner by inserting the prisoner's hands or feet through each loop. The loops are tightened around the prisoner's arms or legs by grasping and pulling on the head portions of the straps. Again, the one-way locking mechanisms within the slots prevent the loops from loosening after they are tightened around the prisoner's arms or legs. The prisoner's arms or legs will be initially spaced by an initial separating distance D. If the prisoner is uncooperative or becomes violent or unruly, the loops of the restraining device can be pulled together by grasping the free ends of each strap and pulling them apart from one another. When the free ends of the straps are pulled apart, the loops are drawn towards one another.

The restraining device can be quickly and conveniently employed by law enforcement officers in place of handcuffs. Because the restraining device is lightweight and inexpensive to produce, a plurality of such devices can be carried by law enforcement officers. This aspect of the invention is particularly useful when the need for multiple arrests arises. Also, because the restraining device is disposable, there is no need to interchange the restraining device when a prisoner is transferred from one law enforcement agency of another.

Other objects and advantages of the present invention will become apparent and obvious from a study of the following description and the accompanying drawings, which are merely illustrative of such invention.

DETAILED DESCRIPTION OF THE INVENTION

Figure 1:
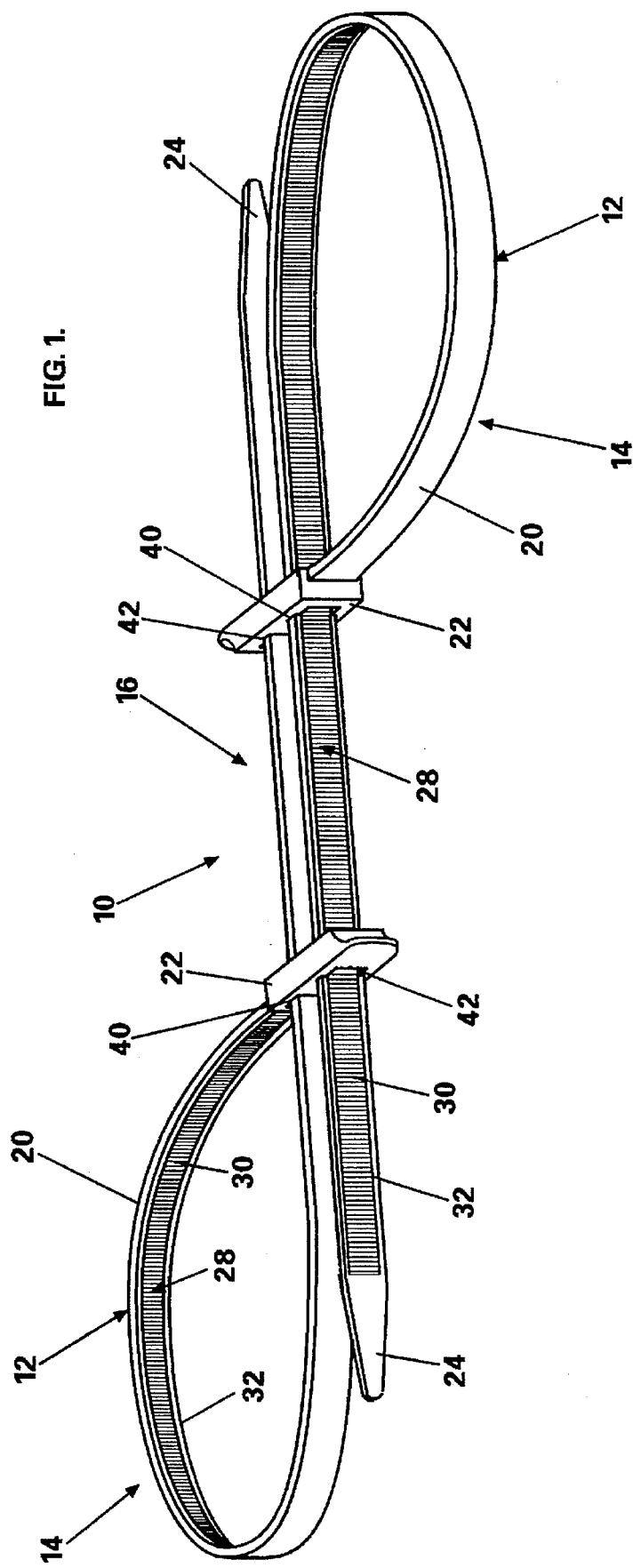
FIG. 1 is a perspective view of the flexible, dual-loop restraining device of the present invention.
Figure 4:
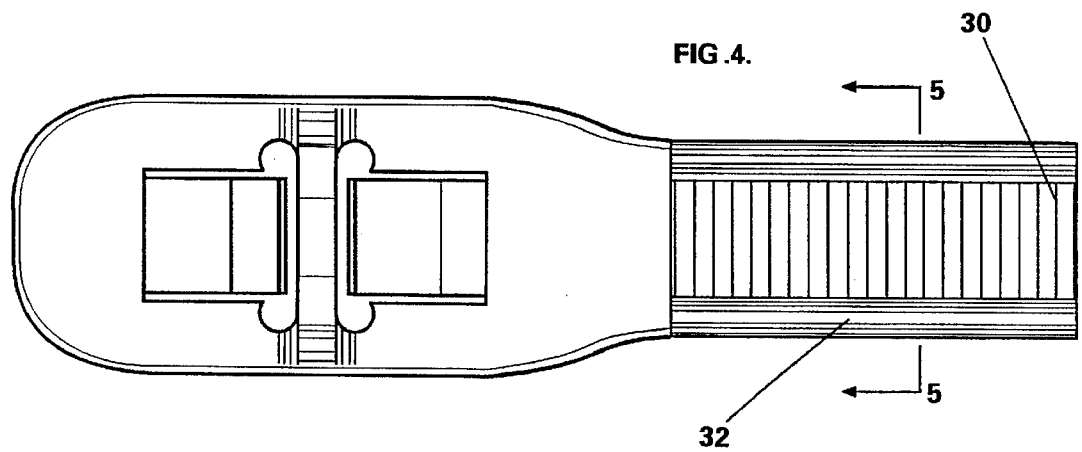
FIG. 4 is a plan view of the head portion of one of the strap elements from the bottom side.
Figure 5:
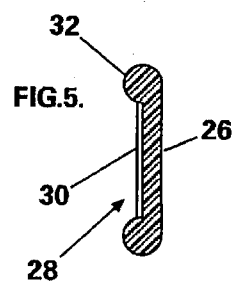
FIG. 5 is a cross-section taken through line 5—5 of FIG. 4.
Figure 6:
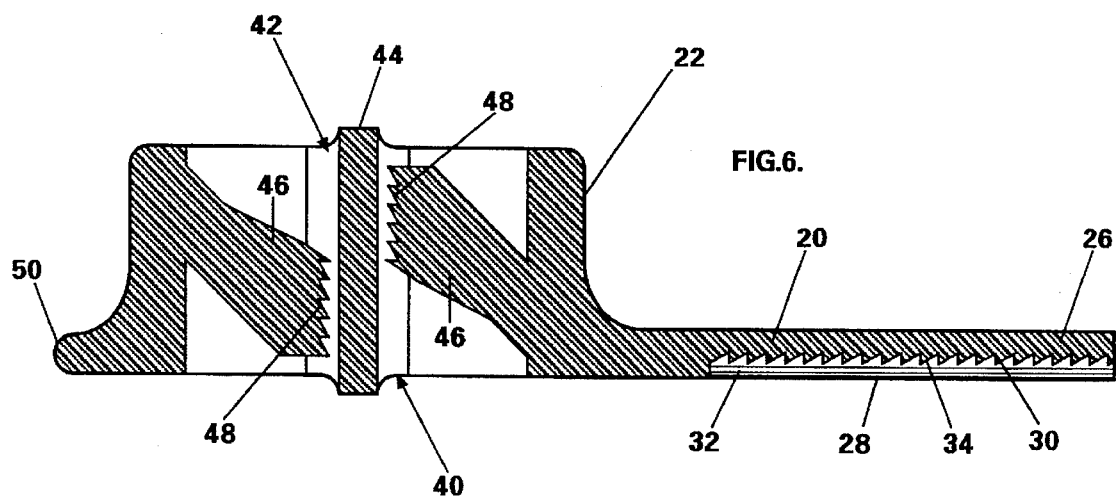
FIG. 6 is a longitudinal section view through the head portion of the strap element taken through line 6—6 of FIG. 3.

Referring now to the drawings, and particularly to FIG. 1, the flexible, dual loop restraining device of the present invention is shown therein and indicated generally by the numeral 10. The dual loop restraining device 10 of the present invention comprises two identical strap elements 12 which are connected to one another. The restraining device 10 includes two restraining loops 14—one formed by each strap element 12—and a connecting section 16 which connects the two loops 14 to one another.

FIG. 1 depicts a preferred embodiment of the restraining device 10 as it is configured for use by a law enforcement officer. The prisoners arms or legs are inserted through the loops 14 of the restraining device 10. The loops 14 are then tightened down against the prisoner's arms or legs. When the loops 14 are tightened, the loops 14 will be separated by a distance D which corresponds to the length of the connecting section 16. If the prisoner resists arrest or becomes violent, the loops 14 can be pulled closer to one another by grasping and pulling on the free ends of the strap elements 12 to draw the loops 14 closer to one another.

Referring now to FIGS. 2–8, the construction of the strap elements 12 is shown in greater detail. For the sake of brevity, only a single-strap element 12 will be described, it being understood that the second strap element 12 is identical in all respects.

Each strap element 12 comprises an elongated, flexible strap 20 having an enlarged head portion 22 integrally formed at one end and a tapered-tip portion 24 at the opposite end. The strap 20 includes a flat top surface 26. A channel 28 is formed in the bottom surface of the strap 20. The channel 28 includes a series of closely spaced, positive locking teeth which are bounded on each side by smooth, rounded rails 32. Each of the teeth 30 includes a sloped camming surface 34, and a substantially vertical locking surface 36.

The head portion 22 includes a pair of slots 40, 42 which extend perpendicular to the strap 20. The slots 40, 42 are separated by a wall 44. Each slot 40, 42 includes a pawl 46 having a series of locking teeth 48 which is designed to engage the locking teeth 30 on the strap 20. The pawl 46 allows the strap 20 to be inserted through the slot 40, 42 in only a single direction. When the strap 20 is inserted through a slot 40, 42, the camming surface 34 of the tooth 30 causes the pawl 46 to flex away from the strap. When a tooth 30 is cleared by the pawl 46, the natural resiliency of the pawl 46 causes it to return to its normal locking position. In this position, the locking surface 32 will be engaged by the pawl 46 thereby preventing the withdrawal of the strap 20. Once the strap 20 is inserted through a corresponding slot 40, 42, the strap cannot be loosened or withdrawn.

The pawls 46 in the slots 40, 42 are oriented to allow insertion of the strap 20 through the slots 40, 42 in opposite directions. The direction of insertion is indicated by the arrows in FIG. 7.

Each strap element 12 is preferably molded as a single piece from a lightweight, thermoplastic material such as engineering grade Nylon or polyurethane. All corners and edges are preferably radiused to ensure that the straps 20 do not cut into the prisoner's skin when tightened.

To use the restraining device 10 of the present invention, each strap element 12 is formed into a loop by inserting the tip portion 24 through the first slot 40 in the head portion 22. After a loop 14 is formed in each strap element 12, the strap elements 12 are then connected to one another by inserting the tip portion 24 of each strap element 12 through the second slot 42 in the head portion 22 of the other strap element 12 as shown in FIG. 1. The restraining device 10 is now ready for use.

The restraining device 10 of the present invention can be employed by law enforcement officers in place of handcuffs or leg irons. The strap elements 12 of the restraining device 10 can also be used individually as a single loop restraining tie. To apply the restraining device 10 to a prisoner, the prisoner's hands or feet are inserted through the loops 14 which are then tightened around the prisoner's arms or legs. The loops 14 are tightened by grasping the head portion 22 of each strap element 12 and pulling it against the prisoner's arm or leg. Once tightened, the loops 14 cannot be loosened. The restraining device 10 can be removed only by cutting the straps 20.

Initially, the connecting portion 16 separates the loops 14 by a predetermined separating distance d. (FIG. 8) For example, for use as a substitute for leg irons, an initial separating distance of approximately 11 or 12 inches is suitable. For handcuffs, an initial separating distance of approximately 4–6 inches is suitable.

If the prisoner resists arrest or becomes violent, the loops 14 can be quickly pulled together by grasping and pulling the free ends 24 of the straps 20. When the free ends 24 of the straps 20 are pulled apart, the loops 14 will be drawn towards one another. In other words, the separating distance d decreases when the straps 20 are pulled apart. Again, the locking mechanism prevents the loops 14 from being pulled apart. The individual strap elements 12 can be formed into loops as described above and conveniently carried in bundles by a law enforcement officer. In this configuration, the strap elements 12 can be quickly and conveniently employed either individually as a single loop restraining device, or as a dual loop restraining device.

The present invention may, of course, be carried out in other specific ways than those herein set forth without departing from the spirit and essential characteristics of the invention. The present embodiments are, therefore, to be considered in all respects as illustrative and not restrictive, and all changes coming within the meaning and equivalency range of the appended claims are intended to be embraced therein.

I claim:

1. An adjustable restraining device comprising:
   (a) first and second flexible straps, each including a head portion at one end thereof and an opposing insert end; wherein said first strap and second strap are distinct from each other;
   (b) a pair of slots formed in the head portion of each of said first strap and said second strap;
   (c) a first loop formed by inserting the insert end of said first strap through a first slot in said head portion of said first strap;
   (d) a second loop formed by inserting the insert end of said second strap through a first slot in said head portion of said second strap;
   (e) said first and second straps being interconnected by inserting the insert end of each strap through the second slot in the head portion of the other strap; and
   (f) locking means to prevent said strap from being withdrawn from said first and second slots in said head portions.

2. The restraining device of claim 1 wherein said locking means comprises a series of teeth formed along said straps and a pawl disposed within said slots for engaging the teeth on said straps.

3. The restraining device of claim 2 wherein said pawl of the locking element is disposed within a slot in the head portion.

4. The restraining device according to claim 3 wherein the locking means in said first and second slots allow one-way movement through said slots in opposite directions.

5. The restraining device according to claim 2 wherein said locking means in the first and second slots allow one-way movement of said strap in opposite directions.

6. An adjustable prisoner restraining device comprising:
   (a) a first strap formed into a first loop of sufficient size to receive a person's limb;
   (b) a second strap formed into a second loop of sufficient size to receive a person's limb; said second strap being distinct from said first strap; and
   (c) an adjustable interconnecting segment coupling said first and second loops together to form a double-loop restraining device; wherein the distance between said first loop and said second loop can be changed by varying the length of said interconnecting segment.

7. The restraining device of claim 6 wherein said first and second straps each include a head portion and an opposing end portion, said first and second loops being formed by engaging the end portion of each strap with the head portion of said strap.

8. The restraining device of claim 7 wherein said interconnecting segment comprises a portion of said first and second strap.

9. The restraining device of claim 8 wherein each strap is slidably engaged with the head portion of the other strap so that the loops can be pulled closer by grasping and pulling the end portions of said first and second straps.

10. The restraining device according to claim 9 wherein the head portion of each strap includes a one-way locking mechanism to allow relative sliding movement of said straps in only one direction.

11. The restraining device of claim 10 wherein said locking mechanisms allow sliding movement of said first and second straps in opposite directions.

12. An adjustable dual loop restraining device comprising:
   (a) a pair of loops with each loop including a one-way locking mechanism that permits the loop to be continuously closed and locked in the process; and
   (b) an adjustable interconnecting segment coupling the two loops together, said interconnecting segment being adjustable for varying the distance between the loops.

13. The adjustable dual loop restraining device of claim 12 wherein the interconnecting segment extends through a second one-way locking mechanism associated with the loops that permit the loops to be moved towards each other and locked against movement away from one another.

* * * * *